(12) United States Patent
Heaton (10) Patent No.: US 10,215,829 B2
(45) Date of Patent: Feb. 26, 2019

(54) USE OF ECHO SHAPES IN NUCLEAR MAGNETIC RESONANCE LOG DATA ACQUISITION AND QUALITY CONTROL

(71) Applicant: Schlumberger Technology Corporation, Sugar Land, TX (US)

(72) Inventor: Nicholas Heaton, Houston, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 193 days.

(21) Appl. No.: 15/142,577

(22) Filed: Apr. 29, 2016

(65) Prior Publication Data

US 2017/0315199 A1    Nov. 2, 2017

(51) Int. Cl.
*G01V 3/32* (2006.01)
*G01R 33/56* (2006.01)
*G01N 24/08* (2006.01)

(52) U.S. Cl.
CPC ....... *G01R 33/5608* (2013.01); *G01N 24/081* (2013.01); *G01V 3/32* (2013.01)

(58) Field of Classification Search
CPC .... G01N 24/08; G01N 24/081; G01N 24/082; G01N 24/084; G01N 24/10; G01R 33/3808; G01R 33/445; G01R 33/448; G01V 3/14; G01V 3/32
See application file for complete search history.

(56) References Cited

U.S. PATENT DOCUMENTS

| | | | |
|---|---|---|---|
| 5,023,551 A | 6/1991 | Kleinberg et al. | |
| 6,121,774 A | 9/2000 | Sun et al. | |
| 6,204,663 B1 | 3/2001 | Prammer | |
| 6,541,969 B2 | 4/2003 | Sigal et al. | |
| 7,126,333 B2 | 10/2006 | Beard et al. | |
| 2002/0153136 A1* | 10/2002 | Kruspe | G01V 3/32 166/250.01 |
| 2011/0234220 A1* | 9/2011 | Mitchell | G01N 24/081 324/303 |
| 2013/0187647 A1* | 7/2013 | Walsh | G01N 24/081 324/303 |

* cited by examiner

*Primary Examiner* — Tung X Nguyen (57) ABSTRACT

A method to process information from a wellbore tool is disclosed having steps of placing a wellbore nuclear magnetic resonance tool in a wellbore to a scan a geological formation, activating the nuclear magnetic resonance tool to send signals to and receive signals from the geological formation, acquiring the received signals from the geological formation wherein the received signals have an echo shape, storing the echo shape according to at least one of a quadrature phase and a nominal signal phase, computing an echo shape from all of the received signals, determining a presence of a noise from the received signals, defining a noise filter based upon the received signals from the nuclear magnetic resonance tool and using the filter to remove noise from the received signals.

10 Claims, 13 Drawing Sheets

USE OF ECHO SHAPES IN NUCLEAR MAGNETIC RESONANCE LOG DATA ACQUISITION AND QUALITY CONTROL

CROSS-REFERENCE TO RELATED APPLICATIONS

None.

FIELD OF THE INVENTION

Aspects of the disclosure relate to recovery of hydrocarbons and the use of downhole tools. More specifically, aspects relate to the use of echo shapes in nuclear magnetic resonance log data acquisition and quality control.

BACKGROUND INFORMATION

Processing of nuclear magnetic resonance signals is an important aspect of hydrocarbon recovery. In order to determine if hydrocarbons are located within a geological stratum, drilling operators place a nuclear magnetic resonance tool in a drill string. Once activated, the nuclear magnetic resonance tool emits a signal or set of signals that penetrate the geological stratum and reflect off different features back to the tool. These signals are subsequently processed to determine if there is a presence of hydrocarbons.

The most common nuclear magnetic resonance data processing methods use so called phase alternating pairs. This method was developed to removing certain noises or "ringing" so that an overall better analysis of the returned signals could be accomplished. In general, conventional methods to evaluate the returned signals seek to increase the signal to noise ratio. Larger and more defined signal components compared with noise, produces more accurate results. Such conventional systems are acquired as weighted sums of digitized nuclear magnetic resonance signals centered around an anticipated echo peak maximum.

In some situations, the actual echo peaks shift compared to the anticipated echo peak maximums. The "window" for the actual signal retrieval will not coincide with the anticipated signal retrieval window. This results in lost signals and improper processing. Conventional systems, therefore leave much to be desired under such conditions and have significant limitations.

Conventional systems undertake certain measures to minimize the error that can be caused by noise. One such method that conventional systems utilize is acquiring successive echo trains for nuclear magnetic resonance signals with alternating phase. The noise, sometimes referred to as antenna ringing, however, is created with constant phase, thus the noise can be identified and eliminated from the returned signal. Thus, the noise generated is not entirely random. This is achieved by alternating the phase of the ninety (90) degree excitation pulse while keeping the phase of subsequent refocusing pulses constant for all trains.

While the above-described method works well for identifying the noise created with constant phase, the conventional systems have a significant limitation. If the noise is not of a constant phase or changes over time, the alternating phase method is less effective, as that method works best with noise that is created with a constant phase.

Other conventional systems estimate a ringing signal by adding specifically designed auxiliary measurements to the nuclear magnetic resonance sequence. Still other conventional systems propose a method to estimate ringing amplitudes either from successive alternating phase Car-Purcell-Meiboom-Gill trains or from auxiliary sequences.

All of the above methodologies apply to amplitudes and amplitude measurement, whether referring to NMR echoes or ringing signals. Ringing filtering and noise reduction are both achieved by combining multiple (at least two) measurements of different phase or frequency.

None of the methods described evaluate or utilize the actual echo shapes received from the reflected signals, instead they rely on assumptions of what will be received and the times that they will be received.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter. A method to process information from a wellbore tool, comprising placing a wellbore nuclear magnetic resonance tool in a wellbore to a scan a geological formation; activating the nuclear magnetic resonance tool to send signals to and receive signals from the geological formation; acquiring the received signals from the geological formation wherein the received signals have an echo shape; storing the echo shape according to at least one of a quadrature phase and a nominal signal phase; computing an echo shape from all of the received signals; determining a presence of a noise from the received signals, defining a noise filter based upon the received signals from the nuclear magnetic resonance tool; and using the filter to remove noise from the received signals.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In the drawings, sizes, shapes, and relative positions of elements are not drawn to scale. For example, the shapes of various elements and angles are not drawn to scale, and some of these elements may have been arbitrarily enlarged and positioned to improve drawing legibility.

FIG. 10 is a graph of mean echo shape and individual bin ringing shapes acquired for different echo spacings in multi-segment measurement.

DETAILED DESCRIPTION

Aspects described provide for using echo shapes in nuclear magnetic resonance log data to ultimately produce higher quality signal recognition and increased signal to noise ratio as compared to using anticipated amplitudes of echo responses. In one example non-limiting embodiment, the method may comprise acquisition of an echo shape, storing of the echo shape according to quadrature phase and nominal signal phase. In the next step, an echo shape may be computed and it is determined if there is ringing in the system. A filter is also defined. Next, integration of echo shape bins is accomplished using an echo shape filter to obtain bin amplitudes. Next, in another example embodiment, compression of bin amplitudes may be performed to singular value decomposition projections. Transmission of projections is accomplished followed by decoding of projections. An inversion may then be accomplished.

The example methodology described above for echo shape processing involves linear operations, therefore the order in which the steps are executed is not critical and may be chosen on the basis of computational efficiency. For that reason, the above order of steps may be modified and is not considered limiting. In other example embodiments, other processing may be used, such as non-linear processing. For illustration purposes and in a non-limiting embodiment, the form of the echo shape filter was not specified in the workflow. In this case, the echo shape filter is defined to be the same as that used for echo amplitude processing, for example a boxcar filter centered on the echo peak maximum as one option.

Figure 1:
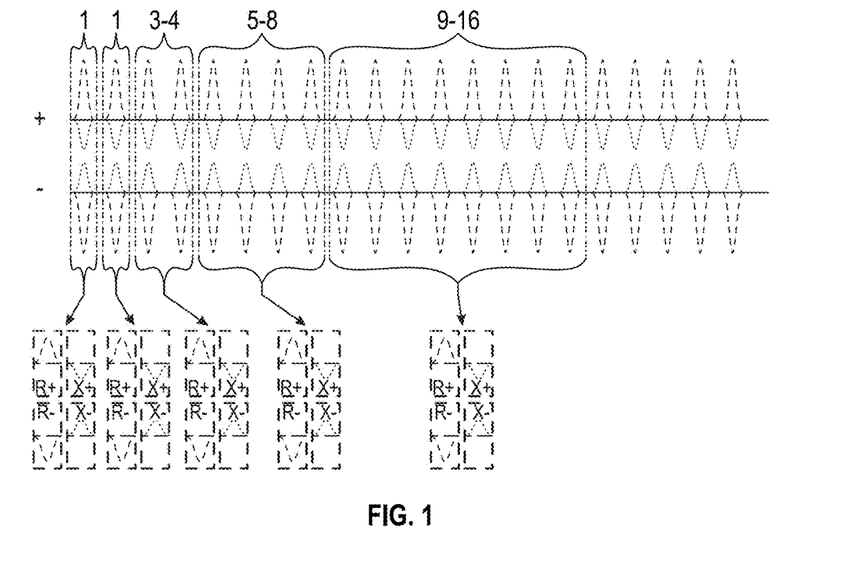
FIG. 1 is a diagrammatic depiction on binned echo shapes.
Figure 2:
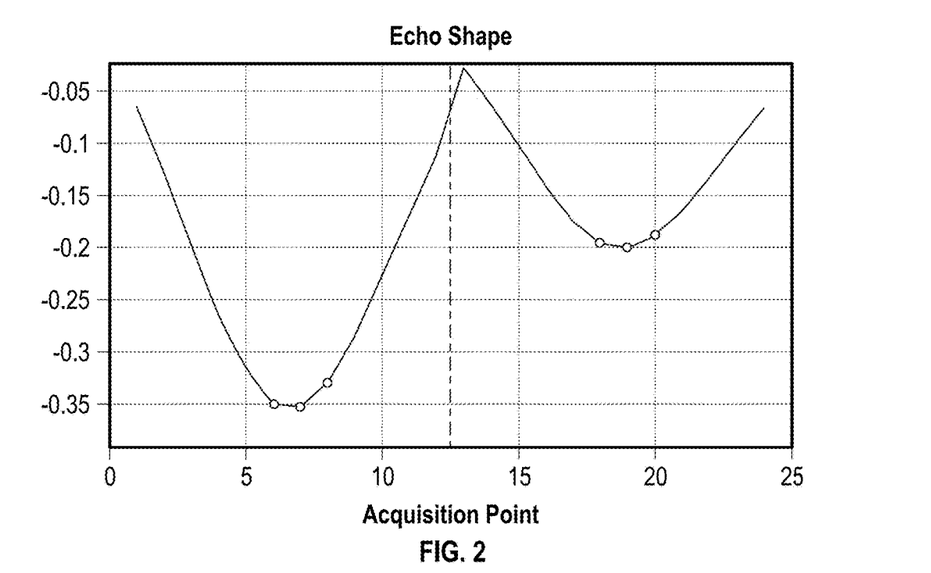
FIG. 2 is a typical echo shape received from a signal returned from a geological stratum.

For a signal contaminated with normally distributed white noise, for instance, the signal to noise ratio is maximized by using a matched filter. For simplicity and description the term "white noise" is used, however other types of noise may be resolved by using this methodology. It is noted that noise, as defined, may include system ringing. For echo shapes, therefore, an echo shape may be used itself as the filter for echo amplitude computation. Referring to FIG. 2, a typical echo shape is presented. As data is typically filtered at acquisition, a conventional matched filter in the time domain may not be optimal in resolving the noise. Treating the echo data in the frequency domain provides insight into the significant components of the signal and noise. To that end, referring to FIG. 3, the lower panel shows the frequency spectra obtained by Fourier transform of the echo shape (blue curve) and the noise spectrum (red curve) computed as the standard deviation of the precision-weighted echo shapes.

Figure 3:
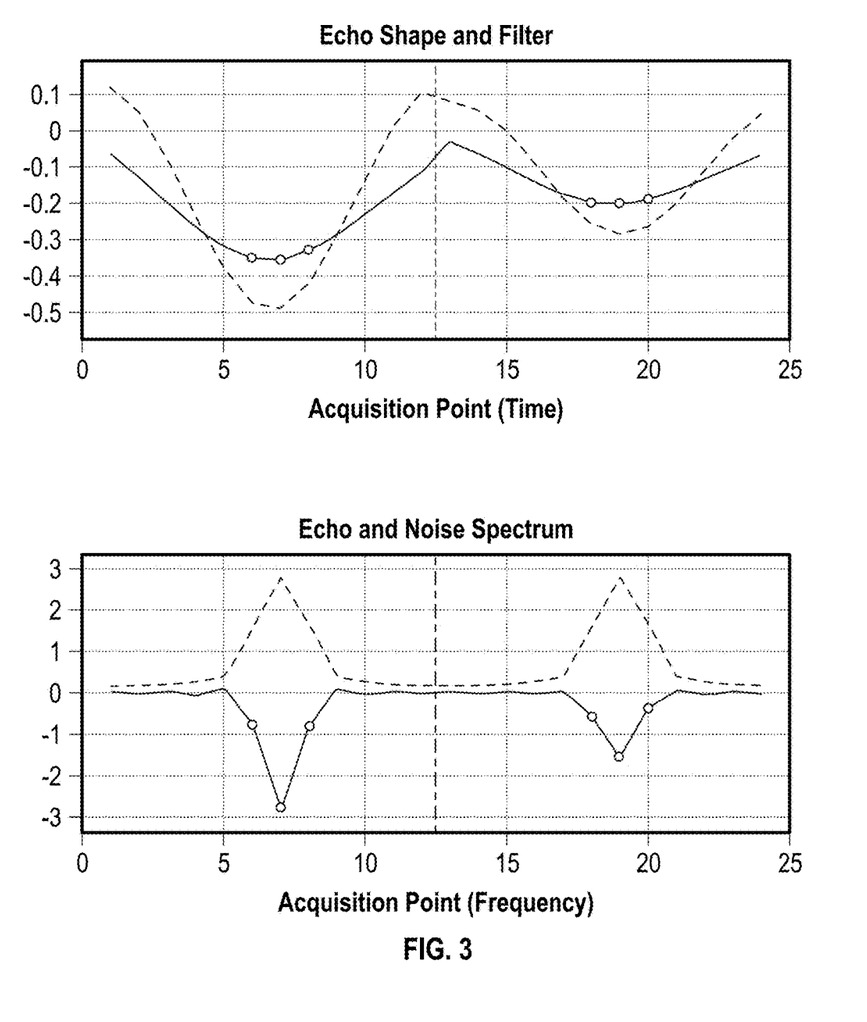
FIG. 3 is an echo shape and noise compensated filter graph series.

For laboratory data, in which the nuclear magnetic resonance signal is identical for all scans, the method described provides a reasonable noise estimate. For logging data, where the signal varies from scan to scan, the noise spectrum can still be computed by first removing the nuclear magnetic resonance echo signal using linear or other fitting methods, making use of prior knowledge of the echo shape. In another embodiment, the noise spectrum is centered about the zero frequency peak (see points #7 and #19). The frequency step per point is approximately 10 kHz. The plots in FIG. 3 show that the nuclear magnetic signal is sharp in the frequency domain and can be well-represented by just three points centered around zero frequency (see points #7 and #19 in frequency plots).

A matched filter in the frequency domain W(v) is defined as:

$$W(v) = \frac{F(v)}{Z(v)} \quad \text{Eq. 1}$$

Where F(v) and Z(v) are the signal and noise spectra respectively. In this case, F(v) is also limited to $|v| \le 10$ kHz (i.e. ±1 point in frequu ncyplot). The equivalent (complex) filter in the time domain w(t), is $$W(t_n) = \frac{\Sigma_m \left(\frac{W(v_m)}{Z(v_m)}\right) e^{-i2\pi t_n v_m}}{\Sigma_m W(v_m) W(v_m)} \quad \text{Eq. 2}$$

The time domain filter corresponding to the frequency domain matched filter is plotted in the top panel of FIG. 3, (corresponding red trace). It is noteworthy that virtually all of the useful NMR and noise information is contained in the 3 complex points of the frequency domain—which are used to define the noise-matched filter). In principle for these acquisition parameters (12 points per echo shape) a factor of 4 reduction in data storage requirements could be gained by recording the frequency domain data instead of the time domain signals.

Figure 4:
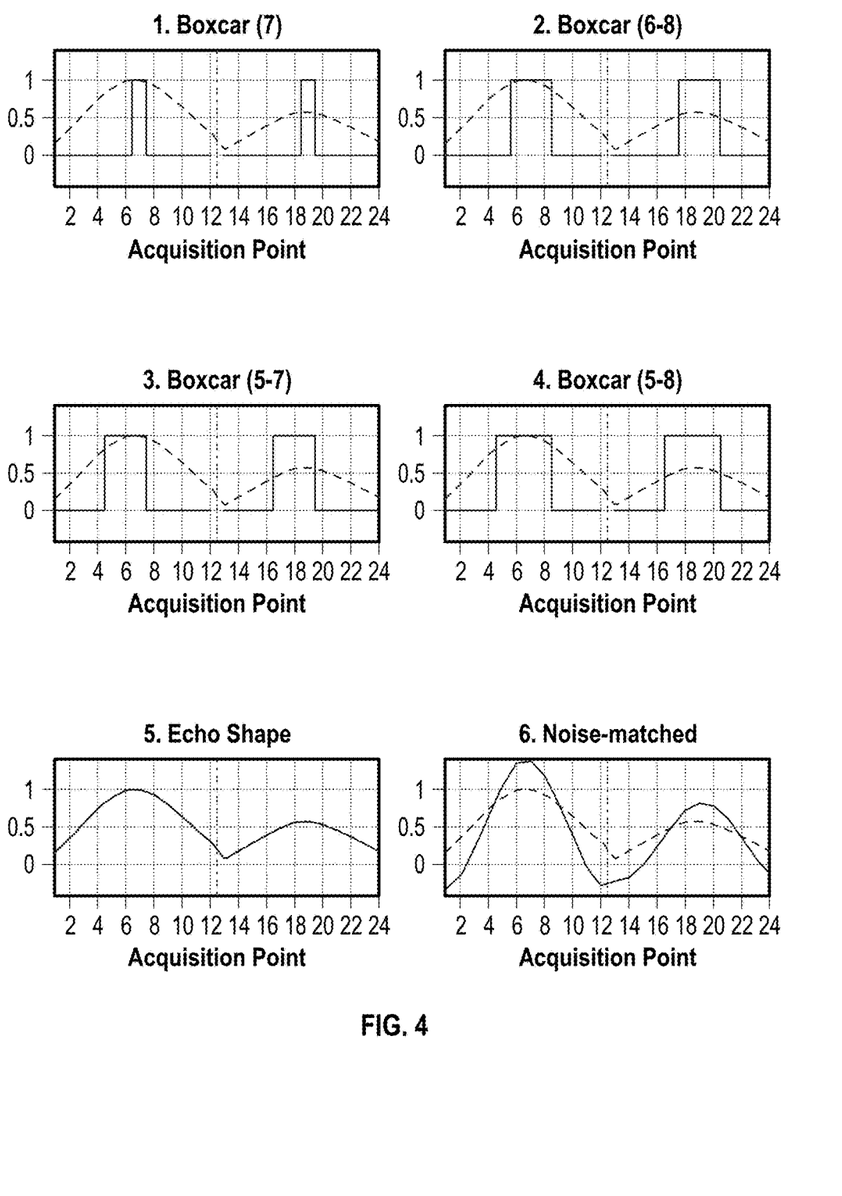
FIG. 4 is a series of echo shape filters and associated typical echo shapes received along a series of acquisition points.

The performance of different filters for the echo acquisition has been evaluated using laboratory data acquired over a range of antenna Q values. The filters evaluated are summarized in Table 1 and plotted in FIG. 4.

TABLE 1

| | FILTER TYPE | POINTS |
| --- | --- | --- |
| 1 | Single Point | 7 |
| 2 | 3 point boxcar | 6-8 |
| 3 | 3 point boxcar | 5-7 |
| 4 | 4 point boxcar | 5-8 |
| 5 | Echo shape | N/A |
| 6 | Noise-matched filter | N/A |

Figure 5:
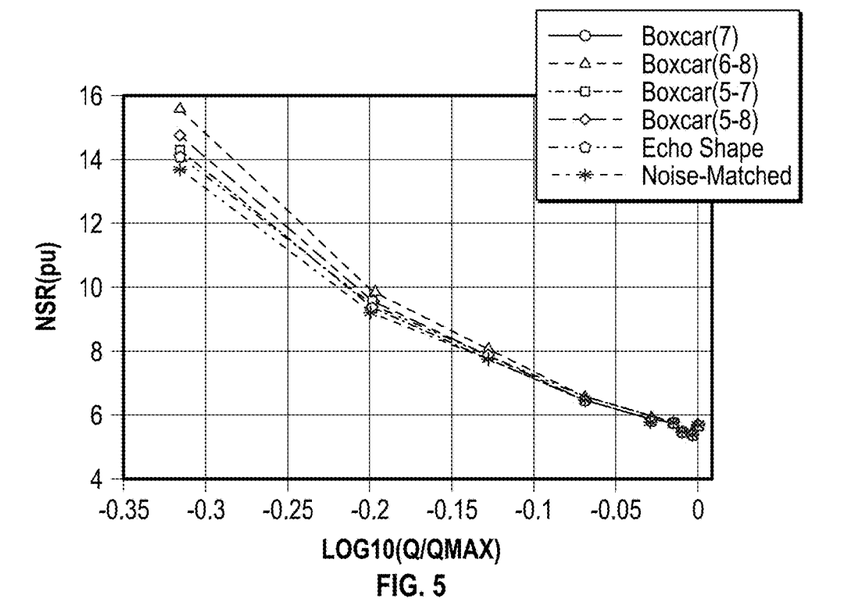
FIG. 5 is a plot of signal to noise ratio as a function of an antenna Q for different filters.

For each of the filters in Table 1, the noise to signal ratio and signal amplitude has been calculated for data acquired over a range of antenna A values. To cover a broad range of environments, the Q values were modified using an external loop with variable resistor around the antenna. The noise to signal variation is plotted in FIG. 5 as a function of $\text{Log}_{10}$ (Q/Qmax). The logarithmic scaling for the Q reference axis in FIG. 5 is used to maintain consistency for the signal plots (see below) which use this choice of scaling to simplify amplitude calibration. The results in FIG. 5 indicate that the choice of echo filter has little impact on noise to signal ratio at high Q (fresh conditions) but is significant at low Q (saline environments). Not surprisingly, the "dynamic" filters based on the measured data (echo shape and noise—matched)

provide the best overall noise to signal ratio performance. Optimal performance at low Q is provided by the noise-matched filter which provides approximately 15% reduction in noise to signal ratio in these conditions relative to the boxcar (6-8) filter used on current EXP tools. The degradation in performance of the boxcar filters with decreasing Q is partly due to the shift in echo maximum.

Figure 6:
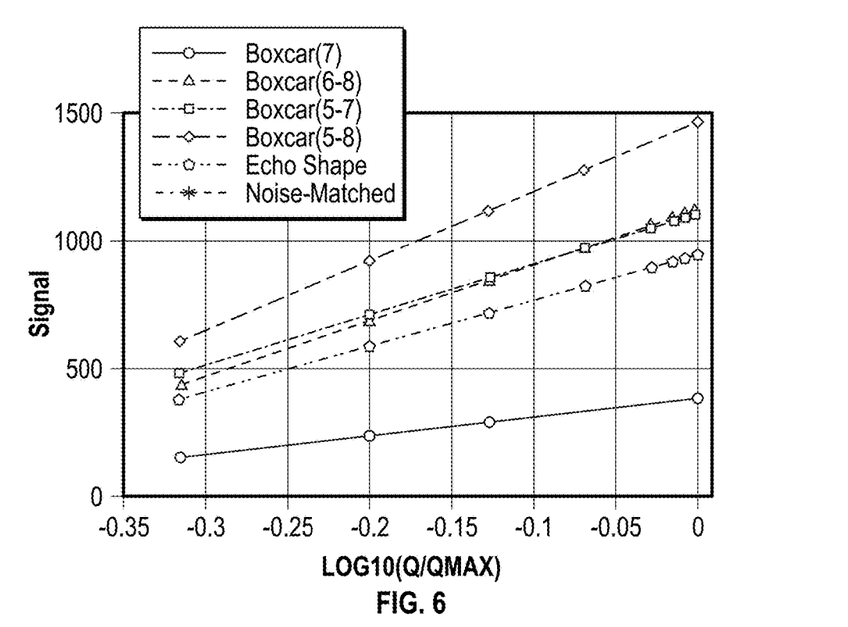
FIG. 6 is a graph of a signal amplitude variation as a function of normalized antenna Q for different filters.

The variation in signal amplitude as a function of $LOG_{10}$ (Q/QMAX) is plotted in FIG. 6. The solid lines are the results of simple linear fits to the data on the logarithmic scale. Although the fits appear satisfactory, there is some variation in the fit quality between the different filters, as summarized in Table 2, which shows the mean and maximum error for each fit. There is no simple physical basis for a log-linear relationship between signal amplitude and Q and it is conceivable that higher order terms are required. With this in mind, a quadratic fit (on logarithmic scale) was attempted and the fit quality results are also summarized in Table 2. As expected, some reduction in fit-error is reported for each of the filters. The greatest improvement is found for the echo shape and noise-matched filters, which provide the best overall performance (lowest mean and max error) with a quadratic fit, although all the filters satisfy typical nuclear magnetic resonance accuracy requirements (3%-5%).

TABLE 2

| | Filter Type | Uncertainty (%) linear | Max Error (%) (quadratic) | Uncertainty (%) (quadratic) | Max Error (%) (quadratic) |
|---|---|---|---|---|---|
| 1 | Single point | 0.6 | 2.1 | 0.4 | 0.8 |
| 2 | 3 point boxcar (6-8) | 0.4 | 2.1 | 0.4 | 0.8 |
| 3 | 3 point boxcar (5-7) | 0.4 | 0.8 | 0.4 | 0.7 |
| 4 | 4 point boxcar | 0.9 | 1.4 | 0.4 | 0.7 |
| 5 | Echo Shape | 0.9 | 2.6 | 0.3 | 0.6 |
| 6 | Noise Matched Filter | N/A | 2.5 | 0.3 | 0.6 |

Figure 7:
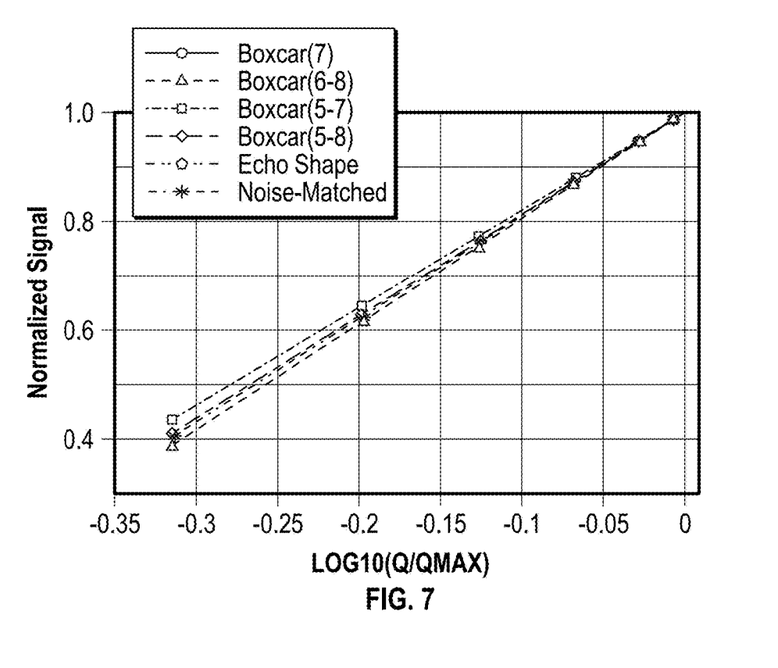
FIG. 7 is a graph of normalized signal amplitude as a function of antenna Q for different filters.

FIG. 7 illustrates the normalized signal amplitude plotted against the logarithm of the normalized antennal Q. The smallest relative variation in signal amplitude over the full range of Q is provided by the boxcar (5-7) filter. This result is consistent with the gradual shift of the echo peak by about one point (approximately 8 us) to earlier time from high to low Q. The differences, however between filters is relatively small, leading to a spread of about 10 percent at the lowest Q.

Systematic Uncertainties Resulting from Echo Shape Processing

Figure 8:
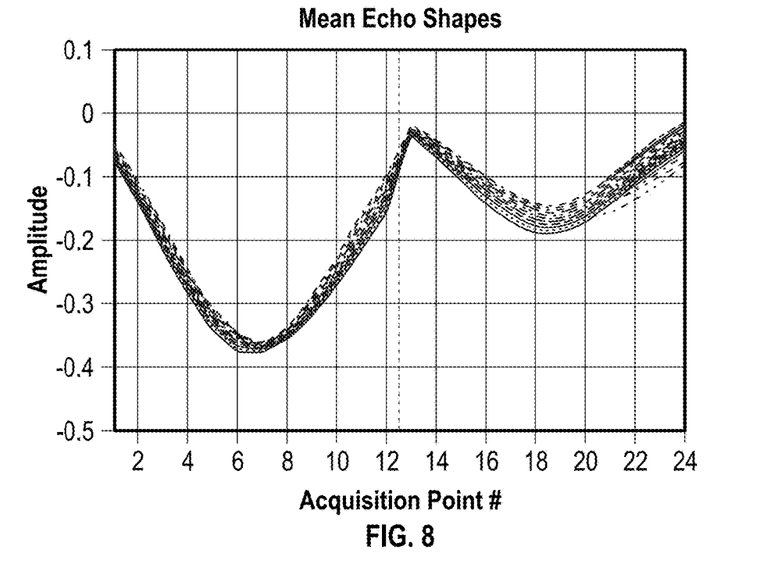
FIG. 8 is a graph of mean normalized echo shapes for a series of different data.

One aspect of shapes processing is the definition of the filter to be used for amplitude computation. This is defined primarily by the echo shape itself. The echo shape is expected to vary slowly from scan to scan, due to the intrinsically weak dependence of shapes on environment and slow variation of the significant environmental variables (borehole resistivity and temperature). Tool noise, however, will affect the echo shape definition and it is important to verify that variations in the computed shape do not compromise ultimate measurement accuracy. The mean normalized echo shape derived at each of 600 scans from a real log set of data is plotted in FIG. 8, along with the mean echo shape (black point sand thick line) for the entire 600 scan dataset. The mean echo shapes at each depth are determined using an averaging window of 21 scans.

A measure of the porosity error induced by the variability in echo shape is provided by taking the projection of each individual echo shape with the overall mean echo shape. The induced percentage signal error for the nth scan is approximately as:

$$\Delta_n(\%)=100(1\ SHAPE_n\ SHAPE_{AVG})\qquad\text{Eq. 3}$$

Similarly a maximum error is defined as:

$$\Delta_{max,n}(\%)=\max[100(1\ SHAPE\ SHAPE')]_n\qquad\text{Eq. 4}$$

Where SHAPE is a matrix of mean echo shapes all scans and $SHAPE_n$ is a vector containing the mean echo shape determined for scan n. This later error estimate (Equation 4) represents the case where the real echo shape and applied echo shape (i.e. filter) for a particular scan are as dissimilar as possible. Although it is a somewhat unrealistic measure of the quantitative error, it can be taken as the absolute worst scenario that would not be exceeded.

Figure 9:
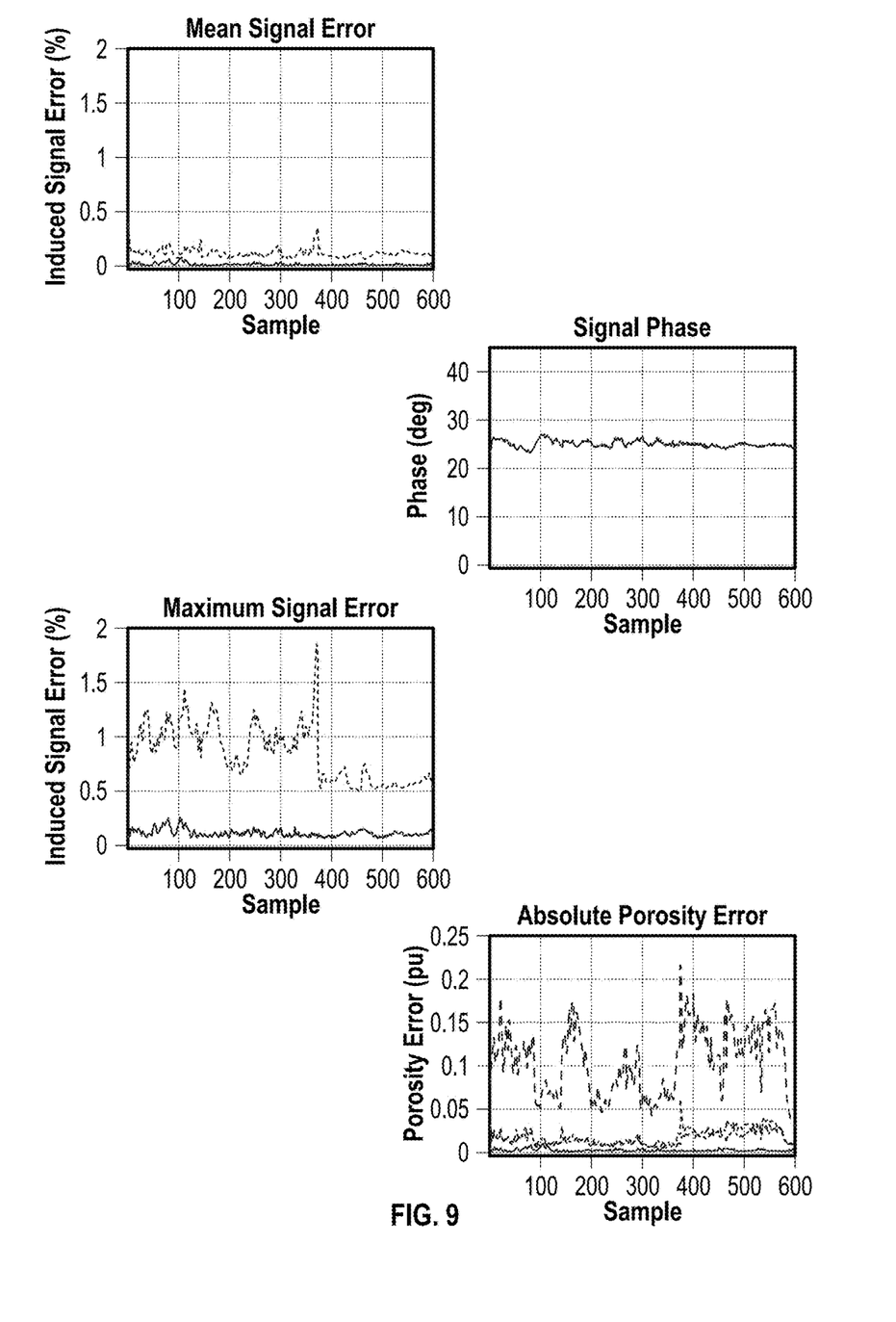
FIG. 9 is a series of data plotted of mean signal error, maximum signal error, signal phase and absolute porosity error plotted over axes of induced signal error percent vs. sample number.

FIG. 9 compares uncertainties in signal amplitude and porosity due to signal error induced by variability in echo shape (red curves) and signal phase (blue curves) for a data set. Note that signal phasing constitutes the analogous part of the preprocessing work flow for conventional amplitude processing. The top left panel corresponds to the mean (best estimate) signal error for echo shape and signal phase uncertainty. The bottom left plot corresponds to the absolute maximum (worst case) signal error. The actual signal phase estimated for the same section of data using standard amplitude processing implemented for a different set of data is plotted in the top right panel. The absolute porosity error (in pu) due to variability in echo shape (red curves) and signal phase (blue curves) is shown in the lower right plot. Solid lines refer to mean (best estimate) uncertainties. Dashed lines correspond to absolute worst case error estimates.

These results indicate that systematic errors induced by variability in the echo shape filter are higher than those induced by signal phase variability but still extremely small. The mean signal error from echo shape variations is less than 0.2% and the corresponding average worst case scenario porosity error is just 0.02 pu for the set of data previously described. The average worst case scenario porosity is just 0.1 pu. It is concluded that the shape induced uncertainty has negligible impact on the overall accuracy budget as defined by tool accuracy requirements. In this non-limiting example embodiment, the accuracy requirements are 3% to 5%. As an alternative to using measured echo shapes to define the average shape, it may also be possible to compute the shape based on model expectations and environmental conditions, such as antenna quality factor and temperature.

Ringing Identification and Filtering

Echo shapes contain information not only about the signal but also about the ringing. Preliminary investigations indicate the potential application of echo shapes to define adaptive filters for ringing suppression. The variability of ringing can be observed by inspection of the "anti-papsed" shapes (i.e. addition of positive and negative phase components). FIG. 10 compares average echo shapes and individual ringing shapes (normalized to single anti-paps) for data acquired using a multi-segment sequence including a 300 us echo spacing segment. The acquisition details are provided in Table 3 wherein the data were obtained with a sensor at 330 kHz.

TABLE 3

| | 1 | 2 | 3 | 4 | 5 | 6 |
|---|---|---|---|---|---|---|
| WT(ms) | 6000 | 1000 | 1000 | 64 | 16 | 4 |
| TE(ms) | 1.0 | 1.0 | 0.3 | 0.6 | 0.6 | 0.5 |

TABLE 3-continued

| | 1 | 2 | 3 | 4 | 5 | 6 |
|---|---|---|---|---|---|---|
| NE | 1024 | 1024 | 256 | 64 | 16 | 8 |
| NR | 1 | 2 | 2 | 16 | 128 | 64 |

Referring to FIG. 10, the data provided demonstrates that the ringing shape is not always constant along the echo trains. For example, in the case of the 0.3 ms echo spacing segment (lower right panel), the variation in ringing is comparable magnitude to the average echo. This result illustrates why simple ringing estimation and subtraction methods are susceptible to errors.

Ringing Filter Concept

As mentioned above, it is possible to determine the pure ringing contribution to shape measurements by "anti-papsing" the positive and negative phase components. If the ringing follows a systematic variation, then there exists the possibility of constructing an adaptive echo shape filter from the observed ringing shapes. A simple approach is attempted here to demonstrate an aspect.

Figure 11:
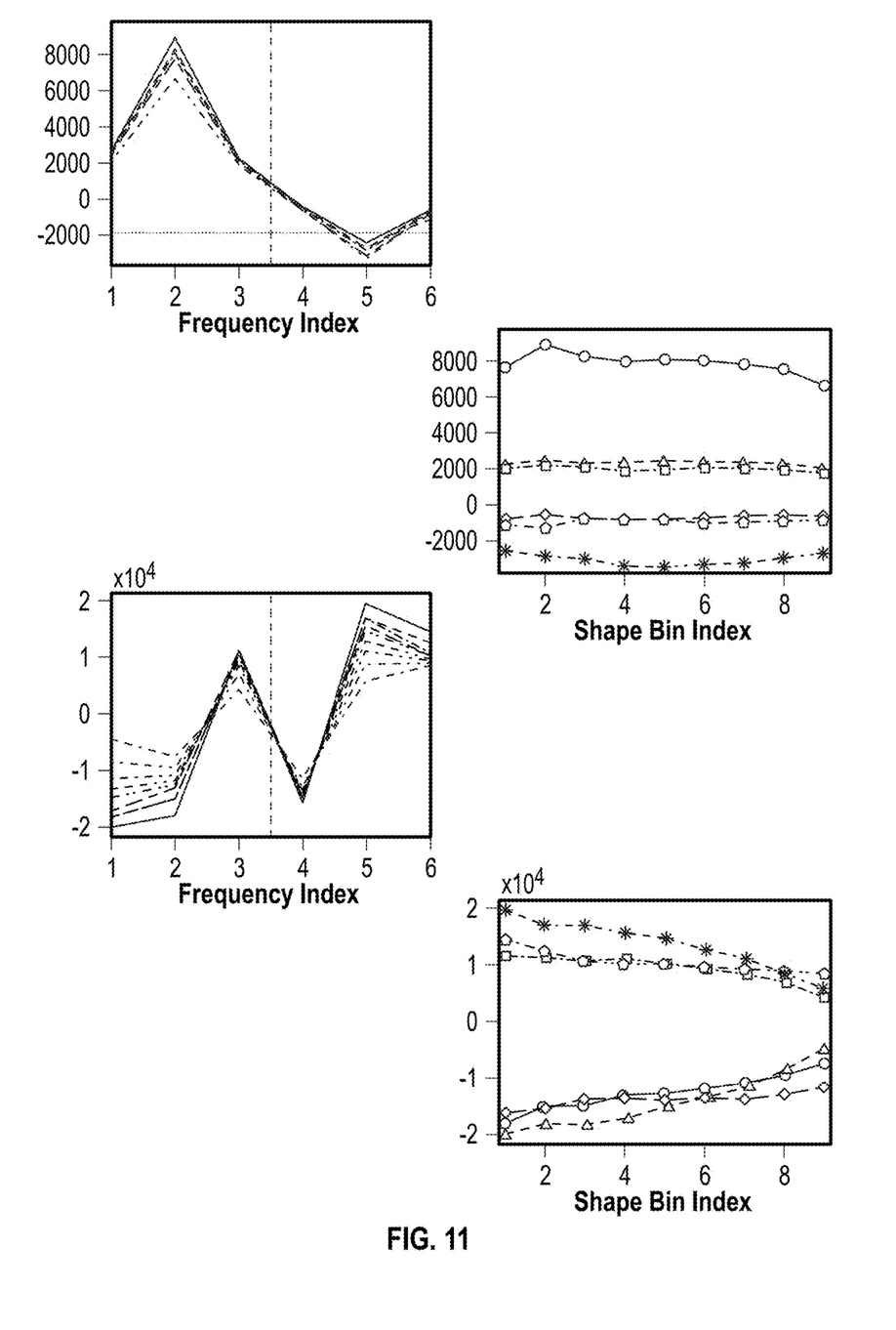
FIG. 11 is a graph of frequency components of echo data and normalized ringing data for a single scan.
Figure 12:
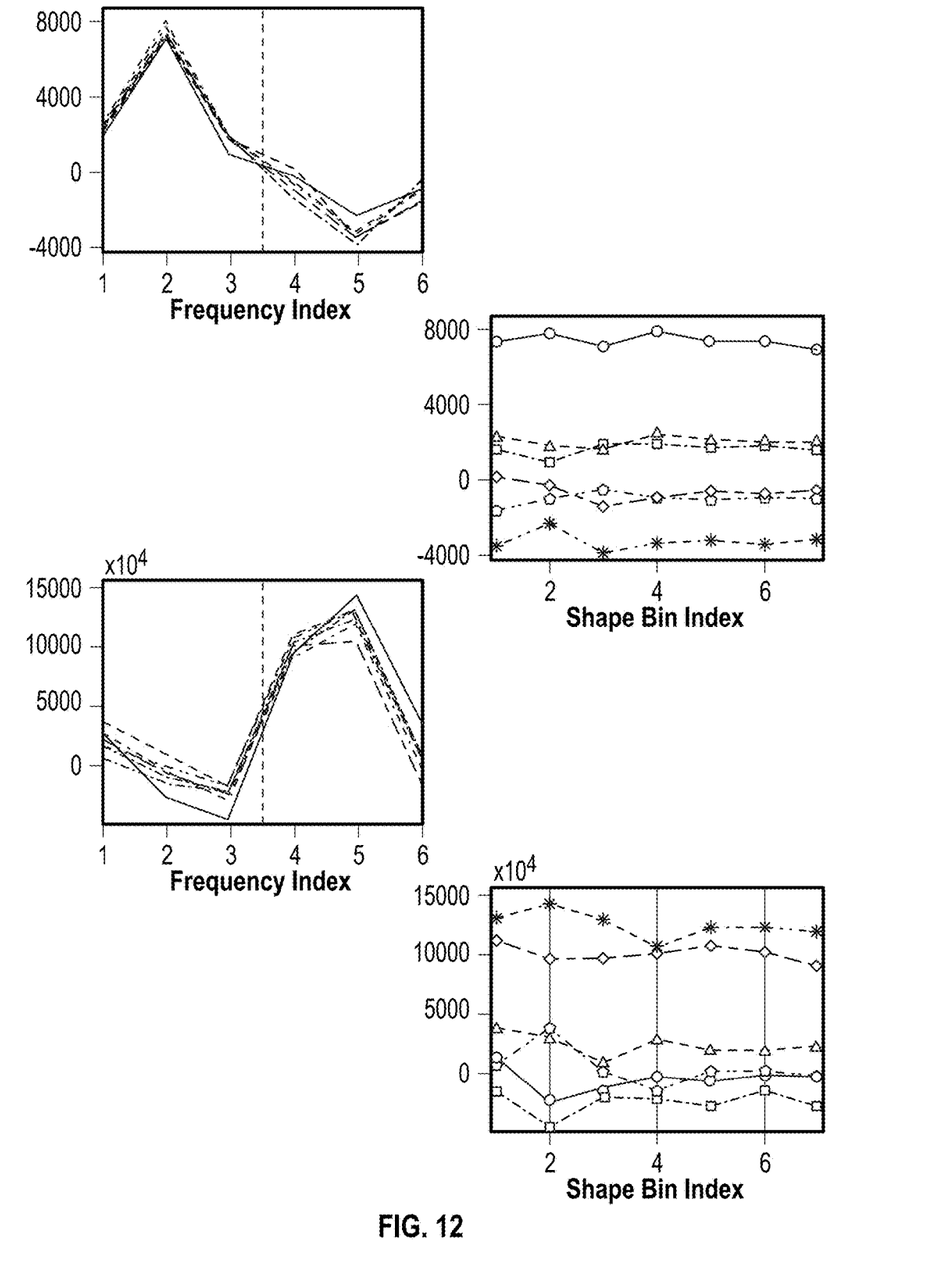
FIG. 12 is a graph of frequency components of echo data and normalized ringing data for a signal scan.

Consider the ringing data for the 300 us segment of the measurement reported in FIG. 10. The (complex) ringing data for this segment comprises 9 vectors of 12 (complex) points which contain the ringing shapes for each of the 9 shape bins. These are plotted in the lower right panel of FIG. 10. In another example embodiment, the same data may be plotted in the frequency domain, as in FIG. 11. The lower right plot in FIG. 11 show that the 300 us ringing shows a systematic variation along the echo train. For stable ringing, no systematic variation is expected, as shown for the 600 us segment of the same acquisition (FIG. 12). For these cases, papsing should effectively cancel the ringing.

For systematically varying data, papsing may provide imperfect cancellation of ringing. If we now assume that the ringing can be represented by a reduced set of (complex) signals, R, the papsed echo shape comprises the pure nuclear magnetic resonance echo plus some contributions from the ringing components, and a random or thermal noise component $\Delta_j$.

$$ECHO_j = A_{echo} ECHO_{SHAPE,j} + \Sigma_k A_k R_{kj} + \Delta_j = \Sigma_i A_i K_{ij} + \Delta_j \quad \text{Eq. 5}$$

Equation 5 constitutes a simple set of linear equations for which the solution is:

$$A = (K \cdot K^T + \lambda H)^{-1} K \cdot ECHO = D \cdot ECHO \quad \text{Eq. 6}$$

$$D = (K \cdot K^T + \lambda H)^{-1} K$$

In equation 6, $\lambda$ is a suppression term and H is the identity matrix with the first element replaced with zero. Increasing $\lambda$ leads to suppression of the ringing components in the resulting filter. A simple echo filter may be defined by keeping just the first element of the amplitude vector. Note that this method may be applied directly in the time domain or frequency domain. The frequency domain has the advantage that noise-weighting is straightforward. The ringing vectors, R, may be selected by various methods. In this demonstration, the principle components of the measured ringing signals are determined using singular value decomposition. This has the advantage of requiring only a small number of terms to approximate all the ringing components. There is no physical basis, however, for the resulting components.

Figure 13:
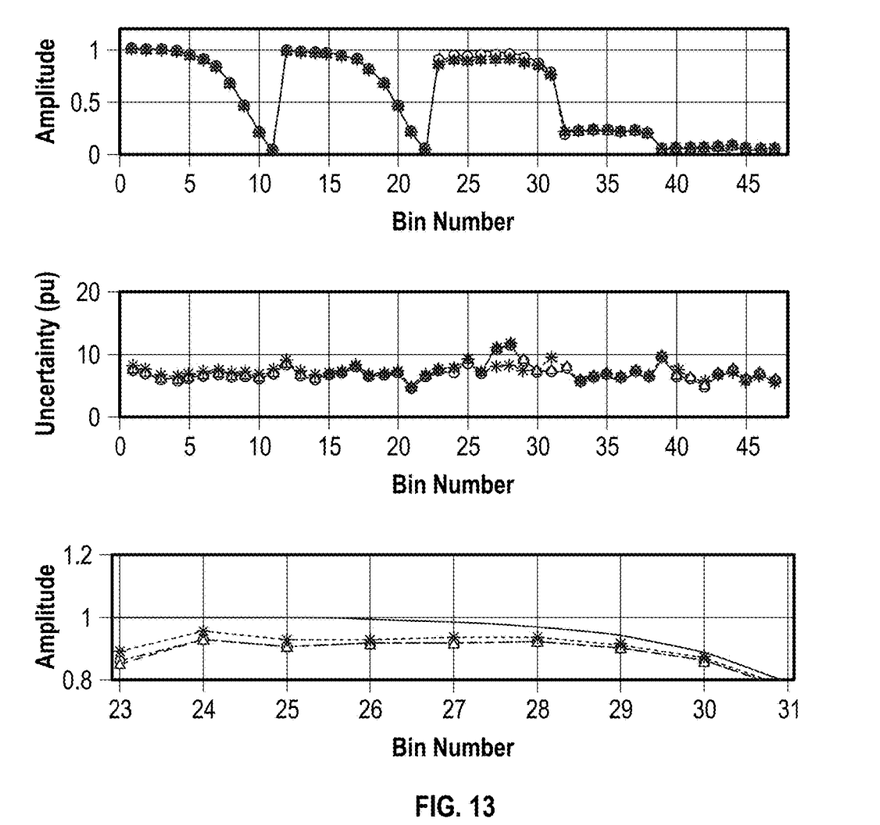
FIG. 13 is a graph of echo amplitudes for different fir different bin numbers as illustrated.

The filter has been applied to the data shown in FIG. 10. For this case, the filter was implemented in the frequency domain and a single ringing component was included in the K matrix. The resulting echo amplitudes for all bins in the acquisition are plotted in FIG. 13. The amplitudes and noise for the 300 us data are slightly improved with the ring filter. The amplitude deficit for this segment is not fully recovered by the filter. In fact part of this deficit may be due to other effects related to receiver response. It is nonetheless encouraging that the ringing filter does provide some measure of improvement with a minimal impact on the measurements with lower ringing. This later observation is due in part to the selection of $\lambda$ which is based on the respective variation in ringing for each segment.

Figure 14:
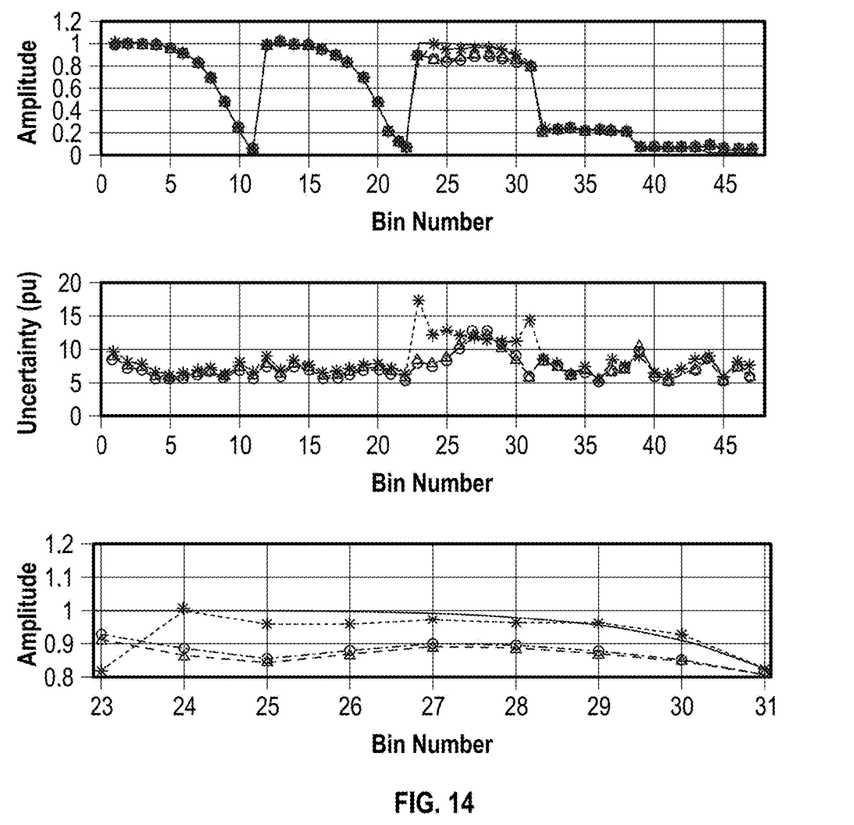
FIG. 14 is a graph of echo amplitudes for a data set with different filters over a number of different BINs.

The same filter has also been evaluated for another dataset acquired with a different sensor. The data is similar to the 300 us data described above, but with a 200 us echo spacing in place of 300 us for segment 3. In all other respects, the acquisition is similar to that described in Table 3. Results are show in FIG. 14. In this example, a noticeable improvement in echo amplitude is observed, but at the cost of some precision in early part of the echo train and a minor degradation of precision in other segments of the echo train. The increased uncertainty for the first echo of the 250 us segment is to be expected since this echo includes 90-ringing components which are not anticipated by the ringing filter.

The results presented above indicate the potential benefit of shape data for ringing suppression. Further improvements in filter efficiency may be achieved using one or more of the following approaches:

Better definition of ringing signal by acquisition of more data prior to the NMR echo Improved filter algorithms Use knowledge of nuclear magnetic resonance response (e.g. multi-exponential decays) to filter ringing from signal.

Use non-linear filters instead of linear algorithms

Echo Quality Control Using Shape Information

By using the echo shapes rather than simply the echo amplitude, an additional measure of data quality can be derived based on the agreement between the measured echo shape and the anticipated echo shape. Two examples of echo shape-based indicator $QC_{1,n}$ and $QC_{2,n}$ are outlined in Equation 7. The first indicator, $QC_{1,n}$ represents a "reverse" correlation parameter and may assume values from 0 to 2, where 0 implies a perfect match between measured echo and the anticipated echo shape. The pre-factor (equal to the echo amplitude) is required to ensure that low amplitude echoes (mainly noise) do not trigger a poor echo quality flag. The second indicator, $QC_{2,n}$ is a simple fit quality indicator. Provided that the echoes are normalized appropriately (as the square root of the total number of echoes contributing to the bin) this indicator should be of comparable magnitude for all bins, and mirror the tool noise $$QC_{1,n} = A_n \times \left(1 - \frac{A_n}{Z_n}\right) \quad \text{Eq. 7}$$

$$QC_{2,n} = \sqrt{\sum_{i=1}^{NPTS} [ECHO(i) A_n ECHO\_SHAPE(i)]^2}$$

$$A_n = \sum_{i=1}^{NPTS} ECHO_N(i)^* ECHO\_SHAPE^*(i)$$

$$Z_n = \sqrt{\sum_{i=1}^{NPTS} ECHO_N(i) ECHO_N(i)}$$

Figure 15:
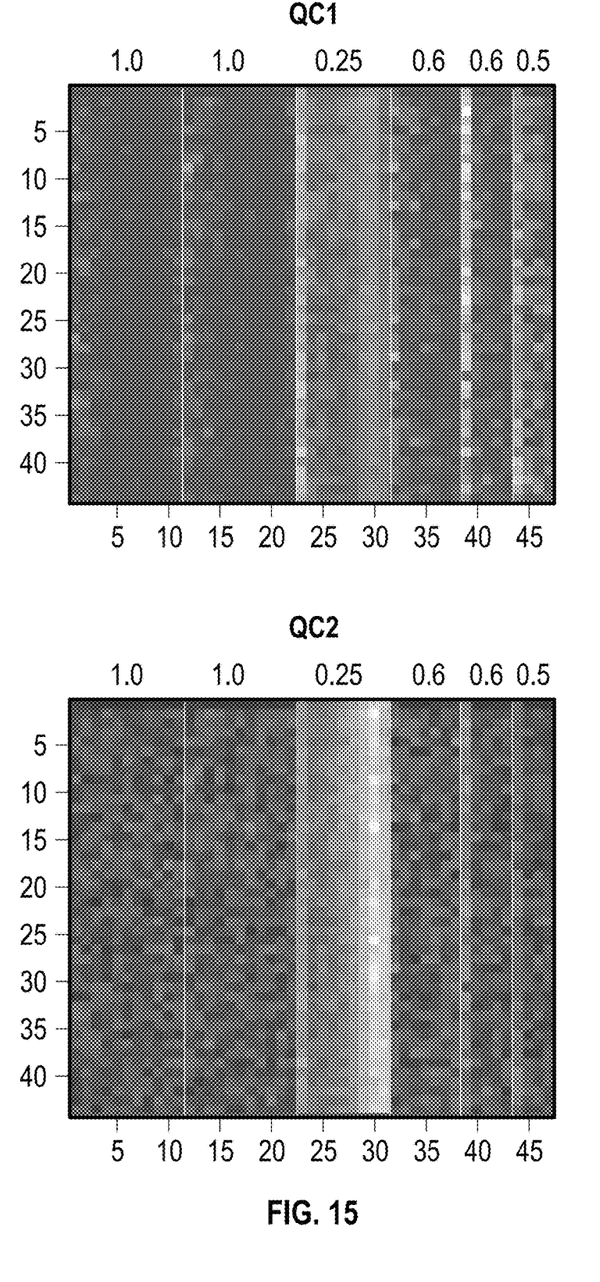
FIG. 15 is a graph of echo quality indicators plotted as a color map.

Referring to FIG. 15, the QC indicators for a laboratory dataset are plotted. The poor quality of the first echo of segment 5 (TE=0.6 ms) is highlighted by the QC indicators Also highlighted is the reduced quality of the 250 us segment (bins 23-31). Note that the average echo shape computation used to generate FIG. 15 omitted the 250 us segment in order to highlight the affected echoes of this segment. The quality indicators described above are to be considered non-limiting examples, wherein other quality indicators may be chosen.

These initial results show that the echo quality indicators provide a useful additional method for identifying early echo quality issues. Unlike existing echo quality indicators the shapes-based algorithm does not rely on any assumptions concerning time variation of the echo amplitude. Note that it is often difficult to distinguish between legitimate rapid signal decay due to short T2 components and genuinely bad echo data. It is also important to recognize that the echo quality indicator implicitly relies on there being a significant difference between the shape of the contaminating ringing signal and the true echo shape. In unfavorable cases, it is possible that ringing and nuclear magnetic resonance echoes coincidentally have similar shapes, in which case the indicator would report "good" quality.

A few example embodiments have been described in detail above; however, those skilled in the art will readily appreciate that many modifications are possible in the example embodiments without materially departing from the scope of the present disclosure or the appended claims. Accordingly, such modifications are intended to be included in the scope of this disclosure. Likewise, while the disclosure herein contains many specifics, these specifics should not be construed as limiting the scope of the disclosure or of any of the appended claims, but merely as providing information pertinent to one or more specific embodiments that may fall within the scope of the disclosure and the appended claims. Any described features from the various embodiments disclosed may be employed in combination. In addition, other embodiments of the present disclosure may also be devised which lie within the scope of the disclosure and the appended claims. Additions, deletions and modifications to the embodiments that fall within the meaning and scopes of the claims are to be embraced by the claims.

Certain embodiments and features may have been described using a set of numerical upper limits and a set of numerical lower limits. It should be appreciated that ranges including the combination of any two values, e.g., the combination of any lower value with any upper value, the combination of any two lower values, or the combination of any two upper values are contemplated. Certain lower limits, upper limits and ranges may appear in one or more claims below. Numerical values are "about" or "approximately" the indicated value, and take into account experimental error, tolerances in manufacturing or operational processes, and other variations that would be expected by a person having ordinary skill in the art.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include other possible embodiments along with the full scope of equivalents to which such claims are entitled. Accordingly, the claims are not limited by the disclosure.

What is claimed is:

1. A method to process information from a wellbore nuclear magnetic resonance tool, comprising:
   placing the wellbore nuclear magnetic resonance tool in a wellbore to a scan a geological formation;
   activating the nuclear magnetic resonance tool to send signals to and receive signals from the geological formation;
   acquiring the received signals from the geological formation wherein the received signals have an echo shape;
   storing the echo shape according to at least one of a quadrature phase and a nominal signal phase;
   computing an echo shape from all of the received signals;
   determining a presence of a noise from the received signals;
   defining a noise filter based upon the received signals from the nuclear magnetic resonance tool; and
   using the filter to remove noise from the received signals.

2. The method according to claim 1, wherein the noise filter is defined using the measured echo shape.

3. The method according to claim 1, wherein the noise filter is defined using a predicted echo shape based on environmental conditions and a model to define the mean echo shape.

4. The method according to claim 1, wherein the noise filter is defined using an averaged echo shape and noise components estimated from the measured data, such as antipapsed data.

5. The method according to claim 1, wherein the normalized echo shape is a weighted mean normalized echo shape.

6. The method according to claim 1, further comprising:
   defining an echo quality control algorithm based on the measured echo shape to perform quality control on the received signals.

7. The method according to claim 1, wherein linear filters are used to process the noise.

8. The method according to claim 1, wherein non-linear filters are used to process the noise.

9. The method according to claim 1, further comprising: integrating echo shape bins using the noise filter and the average echo shape to obtain bin amplitudes.

10. The method according to claim 1, further comprising storing the echo shapes in the bins.

* * * * *